(12) United States Patent  
Wahlgren et al.

(10) Patent No.: US 8,175,718 B2
(45) Date of Patent: May 8, 2012

(54) ELECTRODE PATCH AND METHOD FOR NEUROSTIMULATION

(75) Inventors: Stephen Wahlgren, Easton, PA (US); Anthony DiUbaldi, Jackson, NJ (US); John Young, Staten Island, NY (US); Michael Freeman, Randolph, NJ (US)

(73) Assignee: Ethicon, Inc., Somerville, NJ (US)

( * ) Notice: Subject to any disclaimer, the term of this patent is extended or adjusted under 35 U.S.C. 154(b) by 889 days.

(21) Appl. No.: 11/641,617

(22) Filed: Dec. 19, 2006

(65) Prior Publication Data

US 2008/0147146 A1    Jun. 19, 2008

(51) Int. Cl.
*A61N 1/04* (2006.01)

(52) U.S. Cl. .......................................... 607/61; 607/115

(58) Field of Classification Search ...................... 607/61
See application file for complete search history.

(56) References Cited

U.S. PATENT DOCUMENTS

| | | | |
|---|---|---|---|
| 5,146,926 A | 9/1992 | Cohen | |
| 5,749,912 A | 5/1998 | Zhang et al. | |
| 6,564,079 B1 | 5/2003 | Cory et al. | 600/393 |
| 2004/0088036 A1* | 5/2004 | Gilbert | 607/148 |
| 2005/0277998 A1 | 12/2005 | Tracey et al. | 607/48 |
| 2006/0173510 A1 | 8/2006 | Besio et al. | |

FOREIGN PATENT DOCUMENTS

| | | |
|---|---|---|
| EP | 0910985 A | 4/1999 |
| WO | WO 02/053028 A | 7/2002 |
| WO | WO 2004/002193 A | 12/2003 |
| WO | WO 2004/049937 * | 6/2004 |
| WO | WO 2004/049937 A | 6/2004 |
| WO | WO2004/098703 | 11/2004 |

OTHER PUBLICATIONS

International Search Report dated May 6, 2008.

* cited by examiner

*Primary Examiner* — Eric D. Bertram
(74) *Attorney, Agent, or Firm* — Cheryl F. Cohen, LLC (57) ABSTRACT

A system for stimulating a nerve or nerves in a patient includes an electrode patch having an array of equally spaced concentric electrodes each having a central cathode and a concentrically surrounding anode. The electrode array patch is used to determine the location of the nerve or nerves to be stimulated by electrical pulses. Once the location of the nerve is determined, a concentric electrode patch having a central cathode and a concentrically surrounding anode is positioned at the optimal location on the patient's skin to effect neurostimulation. The concentric electrode patch may be removably affixed to the patient's skin by adhesive or magnets.

6 Claims, 10 Drawing Sheets

ELECTRODE PATCH AND METHOD FOR NEUROSTIMULATION

BACKGROUND OF THE INVENTION

1. Field of the Invention

The present invention relates generally to neurostimulation patches, and more specifically relates to external neurostimulation patches with multiple electrodes.

2. Description of the Prior Art

Neurostimulation is a process by which neurons are stimulated using artificial electrical pulses. A conventional method for neurostimulation includes the use of a pair of planar electrodes separated by a distance. Electric field lines from the pair of planar electrodes are used to stimulate the nerves. Generally, the two planar electrodes are of equal diameter and produce a low intensity electric field over a broad spatial area. Since this low intensity electric field is spread over a broad spatial area, it is less dependent on the exact location of the planar electrodes. The planar electrodes are fixed on the skin with adhesives, or can be implanted beneath the skin.

Currently, the available skin electrodes used for neurostimulation have one or more of the following limitations. Since the electric field of the skin electrodes is spread over a broad spatial area, it results in the electric field having lower intensity. Hence, more power is required to generate an electric field that can stimulate the nerve. Further, skin electrodes are fixed to the skin by means of adhesives. Prolonged ambulatory use of these skin electrodes causes skin irritation due to the adhesives used to fix them to the skin. Finally, because the specific nerve to be stimulated can only be stimulated over a very small area, precise placement of the skin electrodes is essential in order for the electrodes to be therapeutic.

In light of the foregoing discussion, there is a need for a device and method for precise and repeatable placement of skin electrodes, such that neurons surrounding the neuron to be stimulated are least affected. Accurate and repeatable placement of disposable electrodes by a patient outside of the caregiver's office is generally not possible, and this device and method will solve that problem. Further, there is a need for skin electrodes that cause minimal or no skin irritation during prolonged use. Additionally, there is a need for skin electrodes that require less power to stimulate neurons than the skin electrodes that are currently available.

The technology as described in U.S. patent application Ser. No. 11/146,522, filed on Jun. 7, 2005, having as named inventors Michael R. Tracey and Anthony DiUbaldi, and entitled "System and Method for Nerve Stimulation", and further having been published on Dec. 15, 2005 and assigned Publication No. US 2005/0277998A1, the disclosure of which is incorporated herein by reference, is a non-invasive, transcutaneous neurostimulation device, which transmits a controlled, amplitude-modulated waveform. This waveform is composed of a carrier signal and a pulse envelope. The carrier waveform is designed to be of sufficient frequency to overcome attenuation due to tissue impedances. The pulse envelope contains specific pulse width, amplitude and shape information designed to stimulate specific nerves.

The patch is intended to be placed over the sacrum at the level of S2, S3 over the pudendal branch of the sacral nerve. Selectivity is accomplished by the design parameters of the waveform and the spatial location of the patch. That is, neurons of sufficient diameter closest to the patch will be stimulated and neurons of sufficient diameter furthest from the patch will not be stimulated. Therefore, it is critical for the patch to be applied in a location that is spatially closest to the target neuron. This dependency on spatial location can be somewhat mitigated by electrode design. That is, two equal diameter planar spaced electrodes produce a low intensity electric field over a broad spatial area. Conversely, concentric electrode geometry produces a high intensity electric field over a narrow spatial area. The broad electric field pattern will be more tolerant of placement location but will require more power to stimulate the target neuron. The concentric geometry will require less energy to stimulate the target neuron but will be less tolerant to placement error. Therefore, there is a need to design an electrode patch or placement tool that can repeatedly identify the ideal placement location.

U.S. Pat. No. 6,564,079, which issued to Philip C. Cory and Joan M. Cory, the disclosure of which is incorporated herein by reference, describes a sensor system comprising an electrode array and a skin attachment system for use with an electrical field-generating device that can non-invasively detect peripheral nerves and measure conductance at the skin surface. The Cory et al. patent does not, however, describe an array of equally spaced concentric electrodes to detect nerves deep in tissue that can repeatedly identify the ideal placement location.

OBJECTS AND SUMMARY OF THE INVENTION

It is an object of the present invention to provide an electrode patch used to identify the ideal placement location of a neurostimulation electrode patch on a patient to stimulate a nerve or nerves.

It is another object of the present invention to provide a method of minimizing skin irritation caused by adhesion of a neurostimulation electrode patch to a patient's skin.

It is still another object of the present invention to provide a method for non-adhesively attaching an electrode patch to a patient's skin.

It is a further object of the present invention to provide an electrode patch which may be non-adhesively attached to a patient's skin.

It is yet a further object of the present invention to provide a method of identifying the ideal placement location of an electrode patch on a patient's skin.

It is still a further object of the present invention to provide an electrode patch and a method of identifying the ideal placement location of such an electrode patch which overcomes the inherent disadvantages of known electrode patches for neurostimulation and known methods of locating and attaching electrode patches.

An electrode patch formed in accordance with the present invention includes an array of multiple positive concentric electrodes equally spaced from return or negative electrodes. That is, every positive electrode is equally spaced between a concentric negative electrode. This configuration creates a plurality of concentric electrode arrays. This can reduce the placement dependency by placing the electrode array in proximity of the target nerve. The probability of one electrode in the array being in the optimal location increases as the number of electrodes in the array increases. Once the target location is identified, a more concise concentric patch consisting of electrodes can then be placed on the skin for treatment of the intended condition.

The present invention further includes a method of non-adhesive fixation for skin-based electrodes that minimize irritation to skin, such as placement of a metallic disk or disks encased within a biocompatible polymer beneath the skin, or an external skin electrode assembly that incorporates a magnet or magnets and couples to a disk or disks underlying the skin. An alternate embodiment and method of the present invention include the utilization of magnets with opposing poles within the external electrode and within a biocompatible package beneath the skin.

The present invention also includes a method for precise and repeatable patient placement of skin-based electrodes that utilizes a locating tattoo or marking on the skin and a patient placement methodology, which incorporates a rotational scheme in order to minimize skin irritation.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

The present invention describes a system and a method for stimulating a neuron. The system described in the present invention uses skin electrodes 2 for stimulating the neuron 4. The method by which neurons 4 are stimulated, using artificial electrical pulses, is known as neurostimulation, and is described in detail in the aforementioned Tracey et al. patent application Ser. No. 11/146,522, and such description, as well as the circuitry to generate the electrical pulses, and the shape of such pulses, as disclosed in the aforementioned Tracey et al. patent, are incorporated herein by reference. These artificial electrical pulses are delivered to neurons 4 by means of skin electrodes 2, which comprise an anode 6 and a cathode 10. The anode 6 is a negatively charged electrode, and the cathode 10 is a positively charged electrode.

Skin electrodes work on the principles pertaining to electric fields. The strength of the electric field surrounding a source charge is directly related to the quantity of charge on the source charge. Further, the strength of the electric field is inversely related to its distance from the source charge. The electric field extends from the cathode 10 to the anode 6. The electric field, being a vector quantity, is represented by a vector arrow. The vector arrow points in the direction of the electric field, and the length of the vector arrow is proportional to the strength of the electric field. The direction of the electric field is defined as the direction in which a positively charged particle would accelerate when placed in the electric field. Vector arrows are always drawn perpendicular to the surface of the source charge. A higher density of vector arrows around the source charge indicates a higher magnitude of the source charge.

Figure 1:
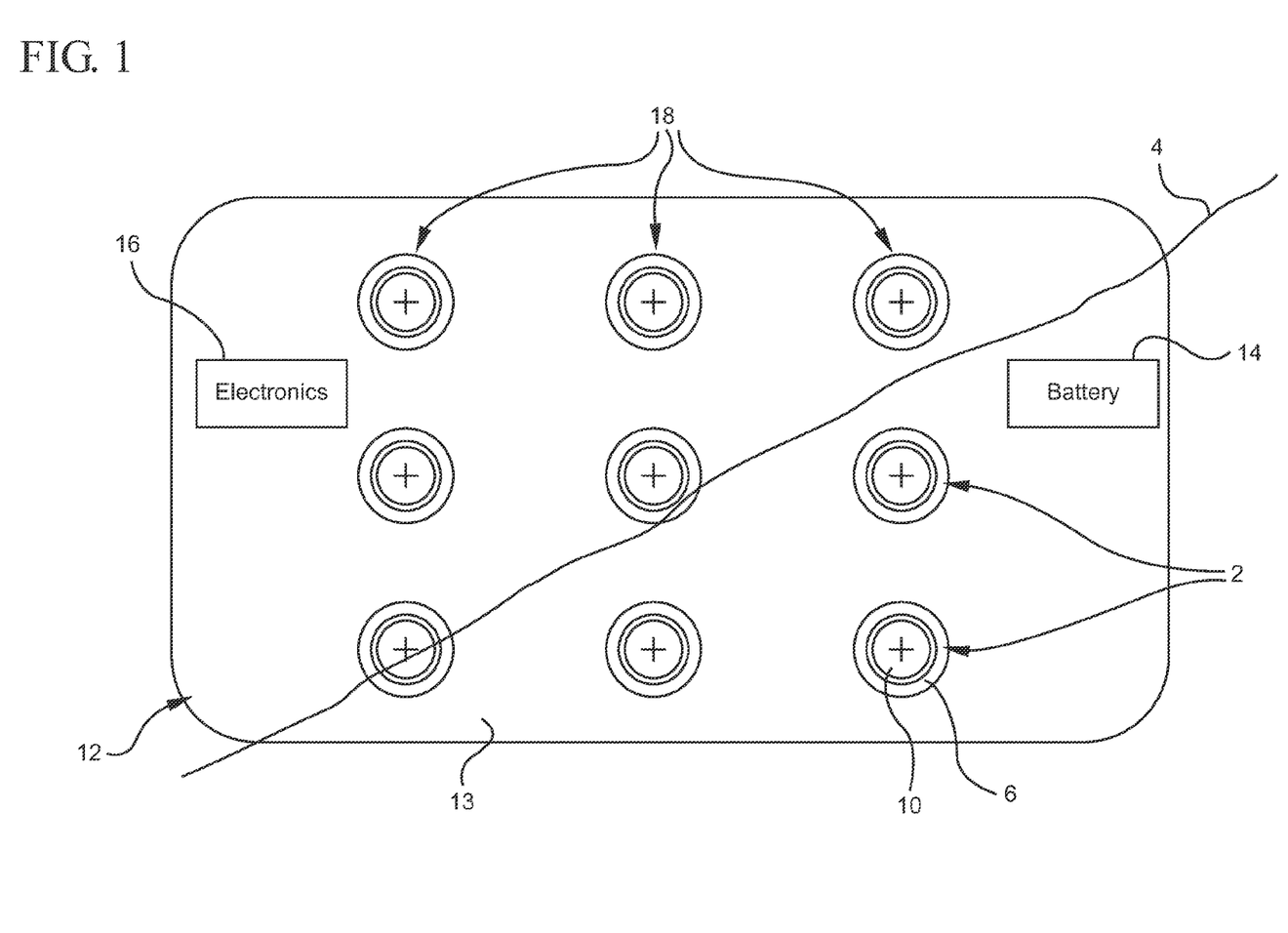
FIG. 1 is a bottom plan view of an electrode patch constructed in accordance with one form of the present invention used for identifying the ideal placement location of a neurostimulation electrode patch on a patient's skin to stimulate a nerve or nerves.
Figure 2A:
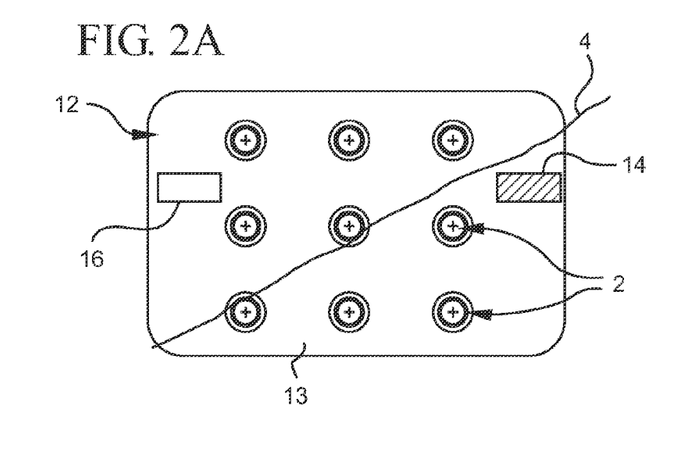
FIGS. 2A through 2D are bottom plan views of the electrode patch of the present invention shown in FIG. 1 and illustrating the sequential excitation of concentric skin electrodes of the electrode patch in identifying the ideal placement location of a neurostimulation electrode patch on a patient's skin to stimulate a nerve or nerves.
Figure 2B:
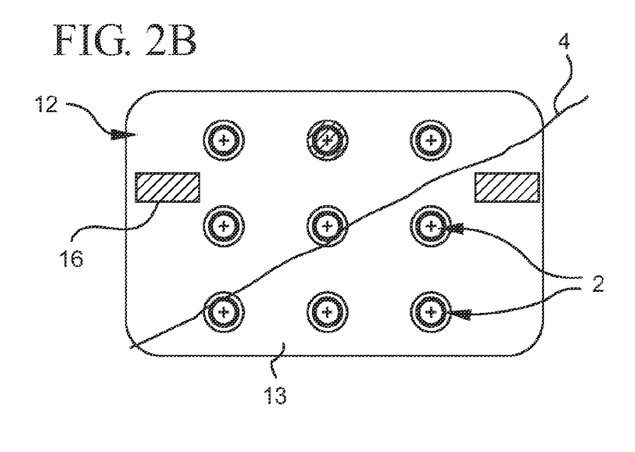
Figure 2C:
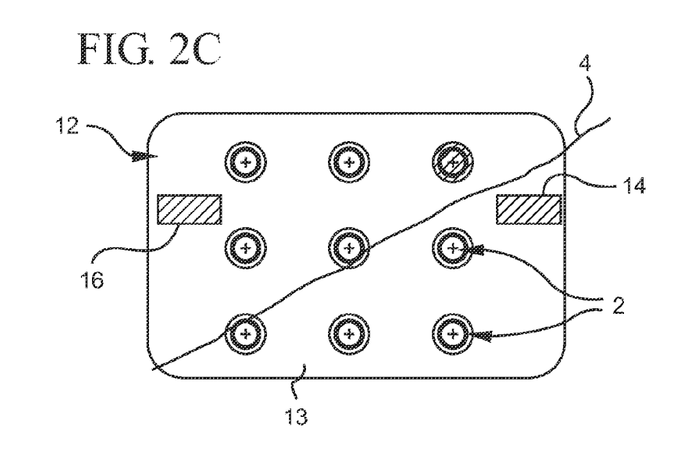
Figure 2D:
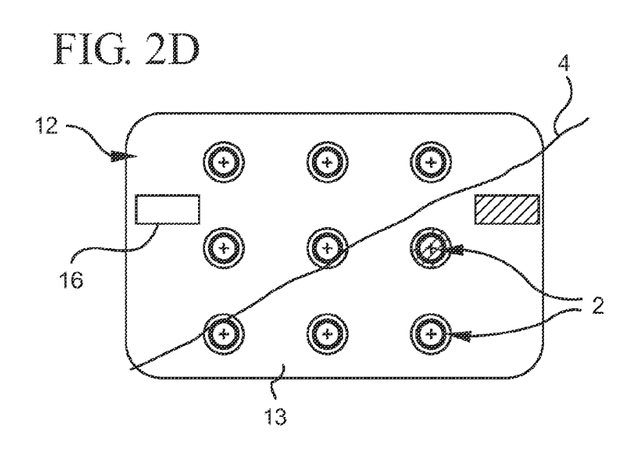

FIG. 1 illustrates multiple concentric skin electrodes 2 in a skin electrode patch 12 formed in accordance with the present invention. The skin electrode patch 12 comprises an array of multiple concentric skin electrodes 2 with equal spacing between the corresponding cathodes 10 and anodes 6, the electrodes 2 being mounted on a supporting substrate 13. Further, a battery 14 that acts as a power source for energizing the concentric skin electrodes 2 is attached to the skin electrode patch 12 and mounted on the supporting substrate 13. The skin electrode patch 12 also comprises electronics 16, such as a stimulation generator, used for controlling the power supplied to each of the multiple skin electrodes 2.

The skin electrode array 18 can be, but need not be, constructed from common electrode materials, such as silver/silver chloride, gold, silver, titanium or any conductive material. In addition, the electrodes 2 can be constructed from conductive polymers, fibers and the like. The electrode array 18 can be fabricated as part of a polyimide flexible circuit, which acts as the supporting structure 13, typical of those standard in industry, or can be stand-alone components that are attached to a stimulation generator (not shown) via cables (not shown). Reference should be had to the aforementioned Tracey et al. published patent application Ser. No. 11/146,522 for a disclosure of such a stimulation generator. In the case where the electrodes 2 are incorporated into the flexible circuit, the flexible circuit would also contain all of the required electronics to generate the stimulation signal. The flexible circuit could also provide mounting features for primary battery cells.

The skin electrode patch 12 stimulates the neuron 4 by means of a non-invasive, transcutaneous neurostimulation technology that is used to transmit a controlled, amplitude-modulated waveform. This controlled, amplitude-modulated waveform is composed of a carrier waveform and a pulse envelope. The carrier waveform has sufficient frequency to overcome attenuation due to tissue impedance. The pulse envelope has a specific pulse width and the amplitude and shape information to stimulate the neuron 4. A disclosure of such an amplitude-modulated waveform is found in the aforementioned Tracey et al. patent application Ser. No. 11/146,522. The skin electrode patch 12 is applied over an approximate region, covering the neuron 4.

As shown in FIGS. 2A-2D, power from the battery 14 is supplied to each electrode 2 of the array 18 in a sequential pattern in order to excite the electrodes 2. The multiple concentric skin electrodes 2 in the skin electrode patch 12 are excited sequentially and out of phase to maintain the desired pulse frequency and to generate a stimulation pattern to detect and locate the neuron 4 to be stimulated. Eventually, a specific concentric skin electrode 2 that is closest to the neuron 4 is excited and the neuron 4 is stimulated. The patient will feel such nerve stimulation and will so advise the technician administering the sequential nerve stimulation test who will record the patient's response and correlate such response with the electrode excited in the sequential test. Alternatively, the patient may wear the electrode patch 12 for an extended period of time, for example, one week. Assume, for example, that the condition that is being addressed is Over Active Bladder (OAB). Each day, a different pattern of electrodes are activated. In this case (i.e., in attempting to alleviate OAB), the patient rather than feeling the nerve stimulation itself could keep a diary as to the frequency and intensity of voiding episodes. The optimum electrode location or locations then correlates with reduced OAB activity recorded in the diary.

Figure 4:
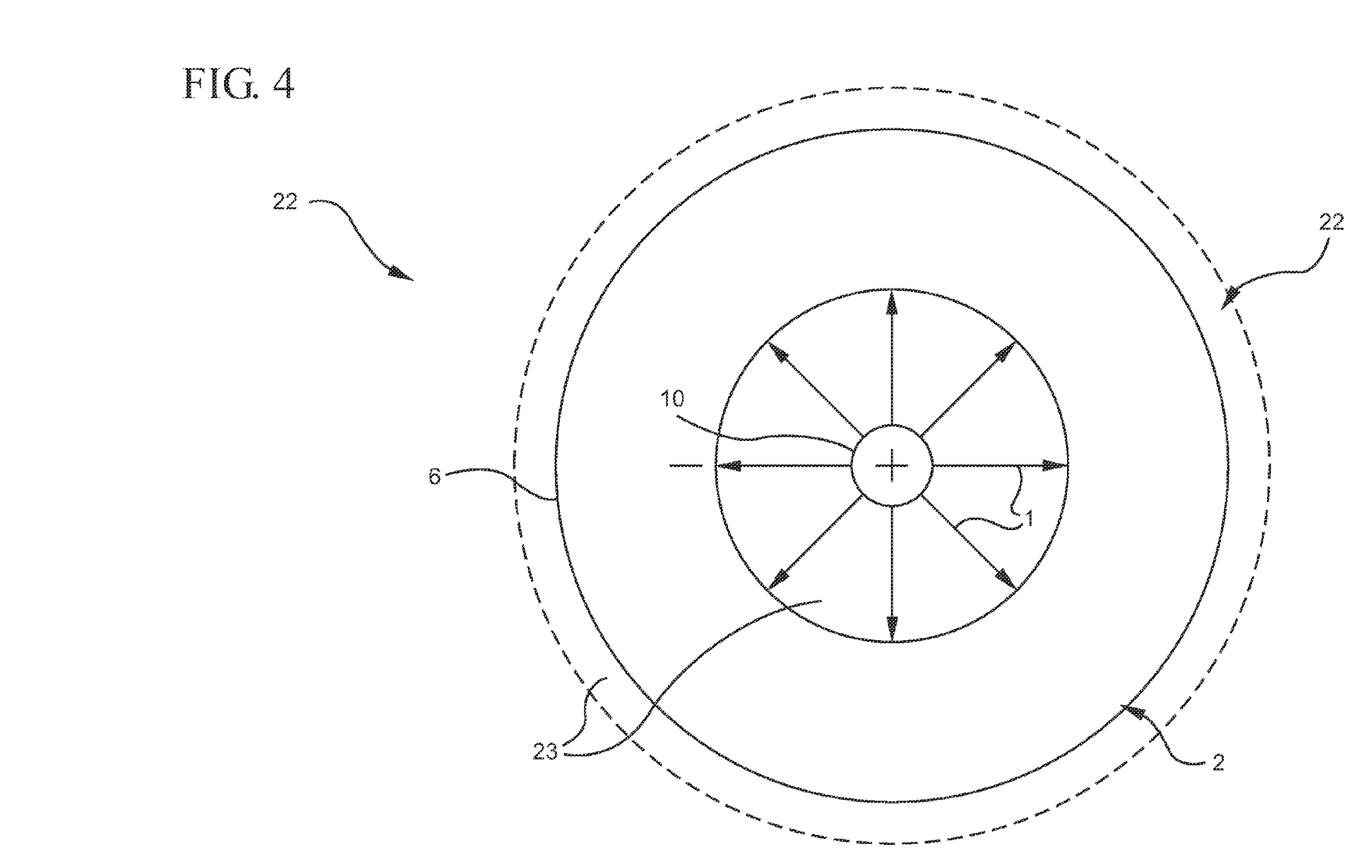
FIG. 4 is a bottom plan view of a concentric skin electrode patch constructed in accordance with another form of the present invention for use in stimulating a nerve or nerves.

This skin electrode patch 12 is particularly useful in a clinic setting in order to determine the optimal location of the neuron 4. In the clinic, a physician or technician can apply the skin electrode patch 12 on a patient such that it encompasses an approximate region covering the neuron 4. Each concentric skin electrode 2 in the skin electrode patch 12 is sequentially excited and the optimal location of the neuron 4 is eventually determined. Once the location of the target neuron 4 is determined, the patient can then be given a smaller skin electrode patch 22 to be placed over the optimal location. In other words, once the neuron 4 has been located, a single concentric skin electrode patch 22 formed in accordance with the present invention can be used to stimulate the neuron 4 further. This smaller electrode patch 22, as depicted in FIG. 4, will be described in more detail below. In addition, the location of the neuron 4 may be marked as a skin tattoo or ink marking 20 to facilitate placement of subsequent patches 22 in ambulatory settings.

Figure 3:
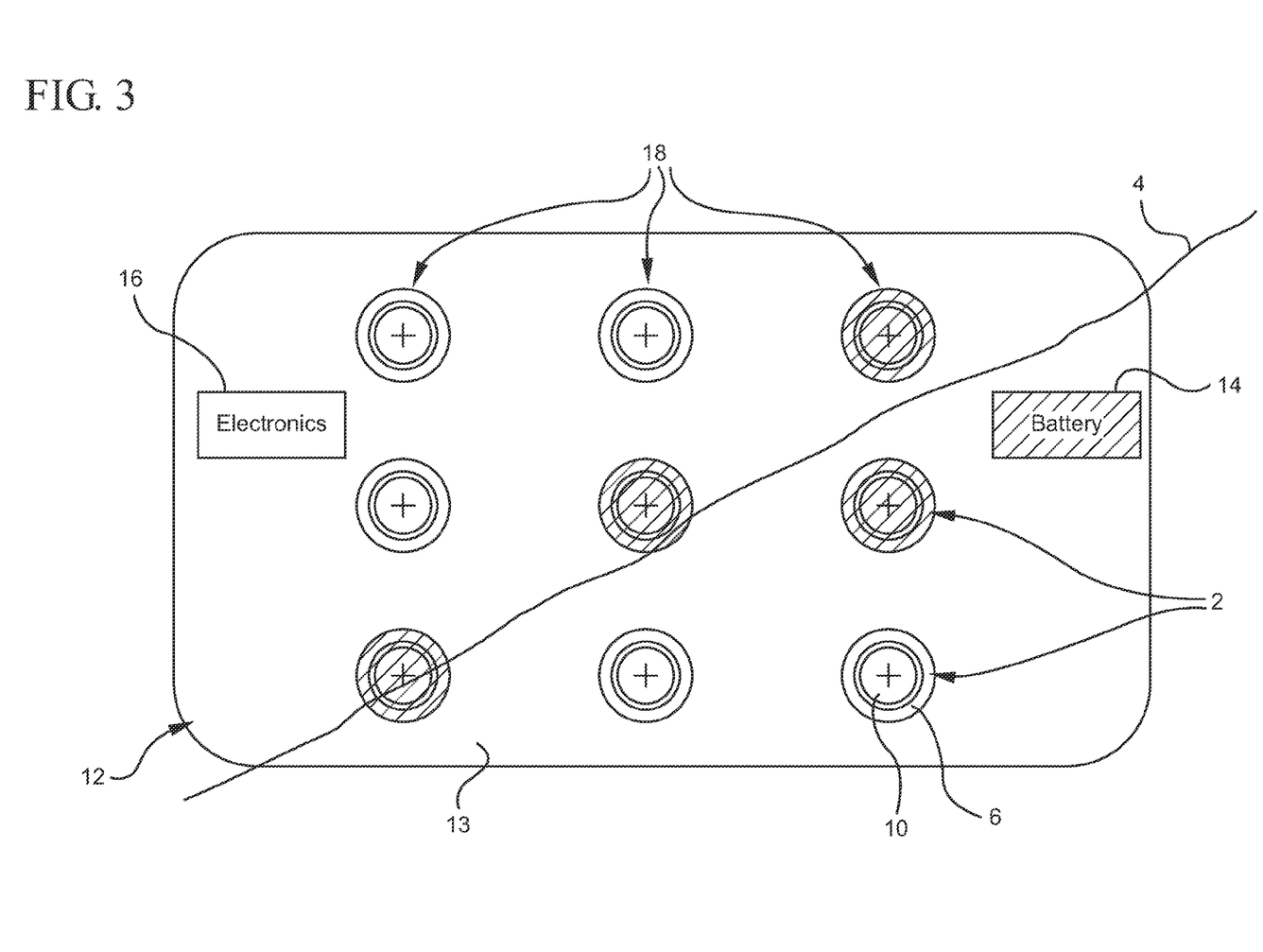
FIG. 3 is a bottom plan view of the electrode patch of the present invention shown in FIGS. 1 and 2A-2D and illustrating the excitation of multiple concentric skin electrodes of the electrode patch to generate a stimulation pattern for identifying the ideal placement location of a neurostimulation electrode patch for stimulation of multiple nerves.

FIG. 3 illustrates the excitation of multiple concentric skin electrodes 2 in the skin electrode patch 12 of the present invention to generate a stimulation pattern in order to stimulate multiple nerves 4 simultaneously. The skin electrode patch 12 comprises a plurality of concentric skin electrodes 2 as described above. Multiple concentric skin electrodes from the plurality of concentric skin electrodes 2 can be energized simultaneously to generate a neurostimulation pattern. This neurostimulation pattern is used to stimulate multiple adjacent neurons 4 as stated above, and can also be used to stimulate multiple fibers in a nerve 4. Once the multiple adjacent neurons 4 have been located, a smaller skin electrode patch 22, which generates the neurostimulation pattern, can be used to stimulate the multiple adjacent neurons further. In addition, as stated above, the location of the neurons 4 may be marked as a skin tattoo or marking 20 (with ink, for example) to facilitate placement of subsequent patches in ambulatory settings.

FIG. 4 illustrates the smaller concentric skin electrode patch 22 of the present invention disclosed previously. The concentric skin electrode 2 may comprise a centrally located cathode 10 and a ring shaped anode 6 concentrically surrounding the cathode 10, although the shape and position of the anode and cathode may be reversed from that described above. The ring shaped anode 6 and the cathode 10 may be mounted on a skin electrode base or supporting structure 23 to form the concentric skin electrode 2. The skin electrode 2 can be, but need not be, constructed from common electrode materials, such as silver/silver chloride, gold, silver, titanium or any conductive material. In addition, the electrode can be constructed from conductive polymers, fibers and the like. The electrode 2 can be fabricated as part of a polyimide flexible circuit, which acts as the supporting structure 23, typical of those standard in industry, or can be a stand-alone component that is attached to the stimulation generator via a cable, as described previously and disclosed in the aforementioned Tracey et al. patent application Ser. No. 11/146,522. In the case where the electrode 2 is incorporated into the flexible circuit, the flexible circuit may also contain all of the required electronics to generate the stimulation signal. The flexible circuit could also provide mounting features for primary battery cells.

Figure 5A:
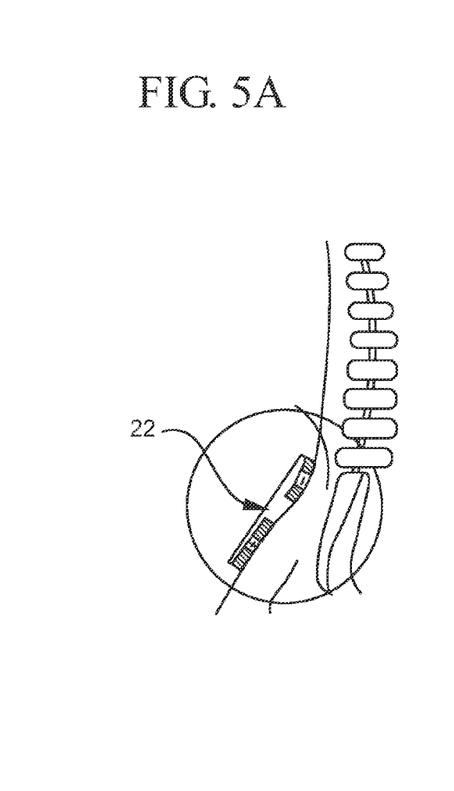
FIG. 5A is a cross-sectional view of an electrode patch constructed in accordance with a further form of the present invention and illustrating its placement on a patient's body to effect neurostimulation.

The concentric skin electrode 2 comprises an anode 6 encompassing a cathode 10 by 360 degrees. The anode 6 and cathode 10 are preferably contained within a transdermal patch 22 or the like, such as shown in one configuration in FIG. 5A, that can be removably secured to the surface of the skin 24. The patch 22 may be any suitable adhesive bandage or the like.

Again with reference to FIG. 4, the electric field between the anode 6 and the cathode 10 of the concentric skin electrode 2 decreases as the spacing between the anode 6 and the cathode 10 increases. Due to this increase in the spacing between the anode 6 and the cathode 10, the impedance increases and the current between the anode 6 and the cathode 10 decreases. As the current between the anode 6 and the cathode 10 decreases, the electric field at the anode 6 and the cathode 10 decreases. The strength of the electric field is related to the ratio of the cathode diameter to the anode diameter. As the cathode diameter decreases, the electric field at the anode 6 decreases and the electric field at the cathode 10 increases. As the diameter of the anode 6 decreases, the electric field at the cathode 10 decreases and the electric field at the anode 6 increases. The increased electric field line density results in a larger electric field. This electric field effect resulting from the variation in the ratio of the cathode diameter to the anode diameter is maximized in a concentric geometry. In the concentric geometry, the anode 6 encompasses the cathode 10 by 360 degrees.

Further, as shown in FIG. 4, the diameter of the cathode 10 is preferably smaller than that of the anode 6 in the concentric geometry. Electric field lines 1 at the cathode 10 with the smaller diameter are closer together, as compared to the electric field lines at the larger anode 6. As a result of the concentric geometry, the electric field line density is significantly higher at the cathode 10. The concentric skin electrode 2 produces a high-intensity electric field over a narrow spatial area. The concentric geometry requires less energy to stimulate a target nerve or neuron 4. However, a single concentric skin electrode 2 is less tolerant to placement error. Therefore, it is important to locate the neuron 4 using the patch 12 with the array of electrodes as described previously and shown in FIG. 1 before placement of this concentric electrode patch 22 in order to avoid placement error.

As described previously, the strength of the electric field is higher at the cathode 10. The concentric geometry of the concentric skin electrode 2 results in a higher concentration of the electric field, as compared to the concentration of the electric field in the case of planar electrodes. This concentration of the electric field in the narrow spatial area results in a reduced power requirement for the stimulation of neurons 4, as compared to the power required for planar electrodes. Further, the concentric geometry of the concentric skin electrode 2 produces a radially symmetric electric field. Due to the radially symmetric electric field, the concentric skin electrode 2 can be rotated without affecting the stimulation of the neuron 4.

Prolonged ambulatory use of conventional skin electrodes causes skin irritation due to the use of adhesives to secure the electrodes to a patient's skin. In an embodiment of the present invention, adhesive is incorporated with the concentric skin electrode 2 as distinct adhesive wells and located around the periphery of the patch 22. As described previously, the concentric skin electrode 2 can be rotated without affecting the stimulation of the neuron 4.

Figures 5B, 5C:
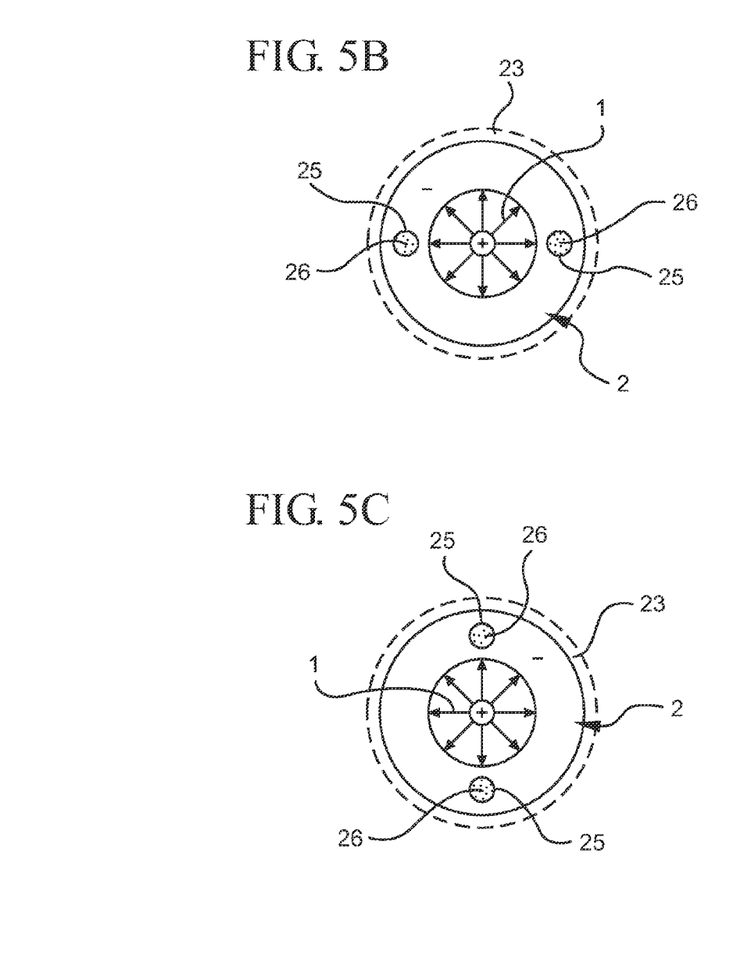
FIGS. 5B and 5C are bottom plan views of the electrode patch of the present invention shown in FIG. 5A and illustrating securing means of the electrode patch in different configurations.

FIGS. 5B and 5C depict concentric skin electrode patches 22 secured to a patient's skin in two separate configurations. Adhesive wells 25 containing an adhesive 26 are situated diametrically opposite one another and are formed directly in the anode 6 or in the supporting substrate 23. The two separate configurations allow the positions of the adhesive 26 to be varied with respect to the skin area on which the concentric electrode patch 22 is applied. However, the electric field lines 1 do not change their pattern from one configuration to the other. Thus, the concentric skin electrode patch 22 can be periodically rotated to change the contact area of the adhesive 26 with the skin, without changing the stimulation pattern. Each time the concentric skin electrode patch 22 is rotated, a distinct area of the skin comes into contact with the adhesive 26. Alternatively, the skin electrode patch 22 can be manufactured so that the adhesive 26 is in varying positions on the patch 22. In this manner, the patient can apply the patch 22 regardless of the position of the adhesive 26, and the adhesive 26 will be in a different position on the skin due to the varying position of the adhesive 26 on the patch itself 12.

Figure 6:
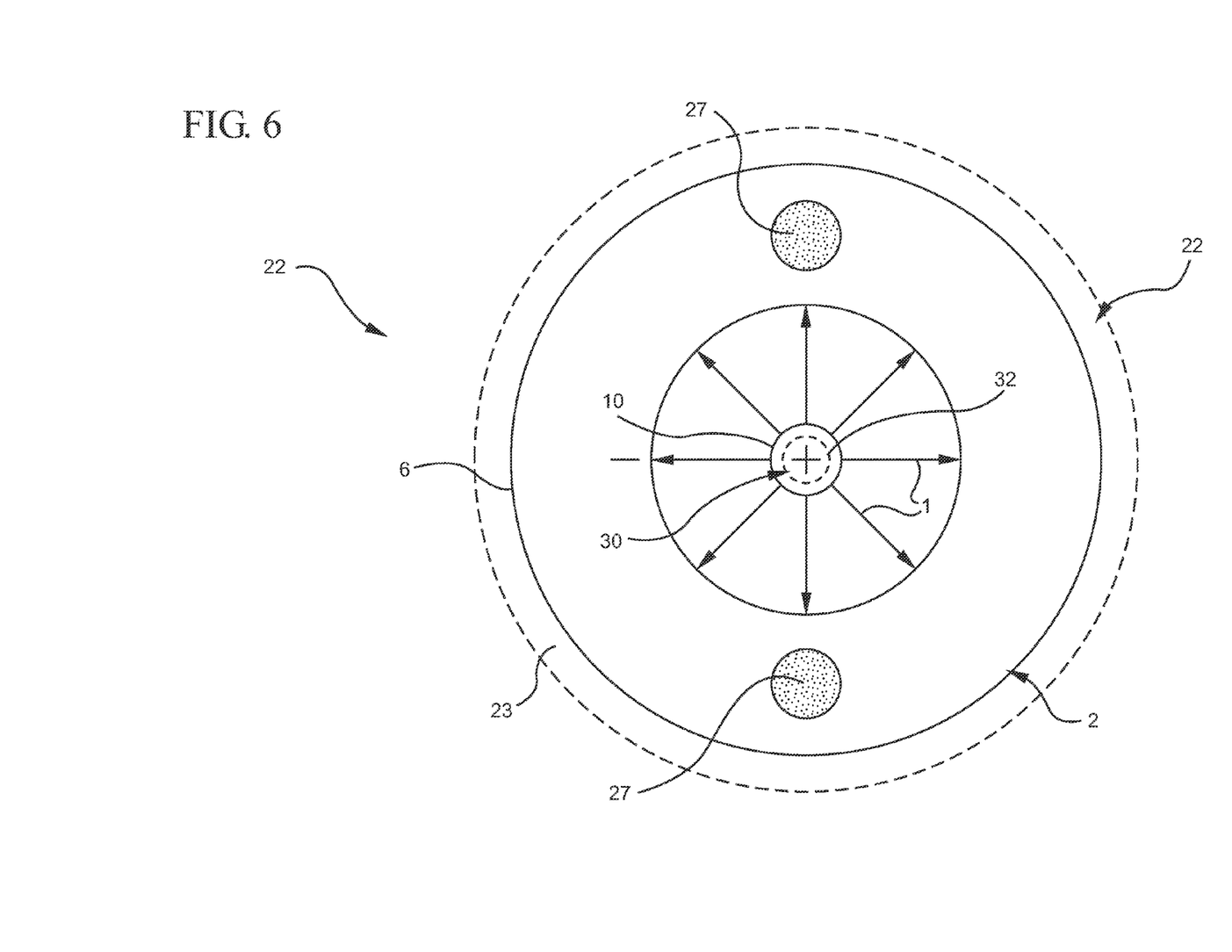
FIG. 6 is a bottom plan view of a concentric skin electrode patch constructed in accordance with yet another form of the present invention and having means for facilitating the proper positioning of the electrode patch on the skin of a patient.

As described previously, once the location of the target neuron 4 has been determined using the electrode array patch 12, a smaller patch 22 can then be placed on the optimal location. However, repeatable precise placement of the patch 22 may be difficult due to human error. In this instance, a skin tattoo or marking 20 (such as with ink) depicting the optimum placement of the patch 22 may be useful. FIG. 6 illustrates a concentric skin electrode patch 22 with means for positioning the patch over the skin tattoo or marking 20. The concentric skin electrode patch 22 includes two securing means 27 to secure the concentric skin electrode patch 22 to the skin. Examples of securing means include adhesives 26, metal discs 30 and magnets 28. Adhesives 26 can be directly secured to the skin. Further, the concentric skin electrode patch 22 includes a central cutout 32 preferably formed through the thickness of the cathode 10 (and possibly any supporting substrate 23) for viewing the skin tattoo or marking 20, which helps in precise and repeatable placement of the concentric skin electrode patch 22 on the patient's skin in the desired location.

Figure 7A:
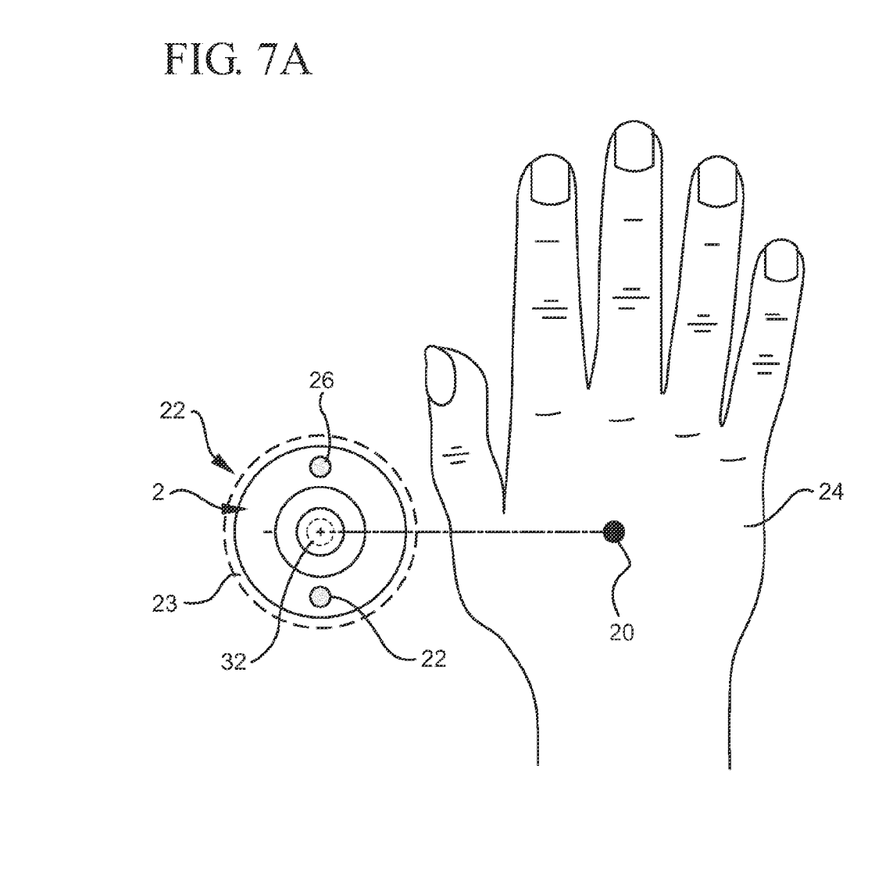
FIGS. 7A and 7B are respectively bottom and top plan views of the concentric skin electrode patch of the present invention shown in FIG. 6 and illustrating the method of properly positioning and affixing the electrode patch on the skin of a patient.
Figure 7B:
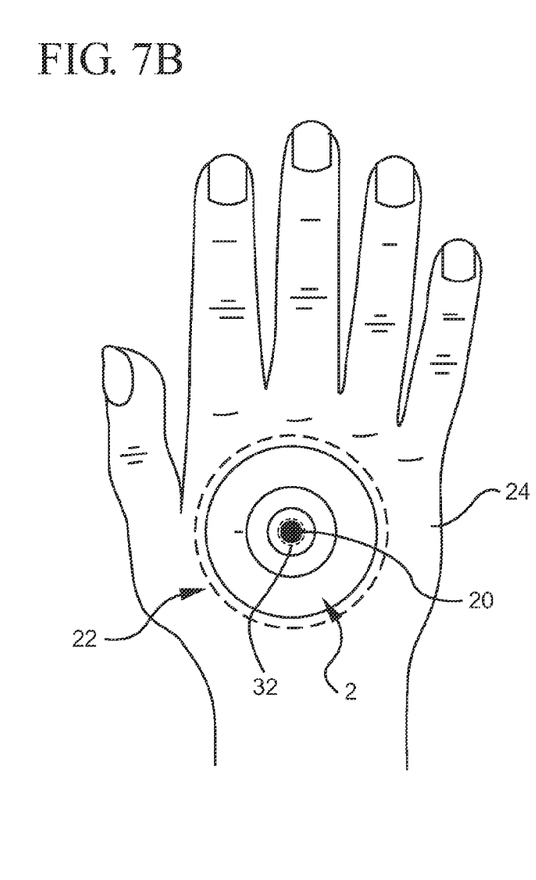

FIG. 7 illustrates placement of the central cutout 32 of the concentric skin electrode patch 22 over the skin tattoo or marking 20 so that the marking 20 is aligned with and viewable through the cutout 32. The adhesive side of the concentric skin electrode patch 22 faces towards the skin.

Figure 8:
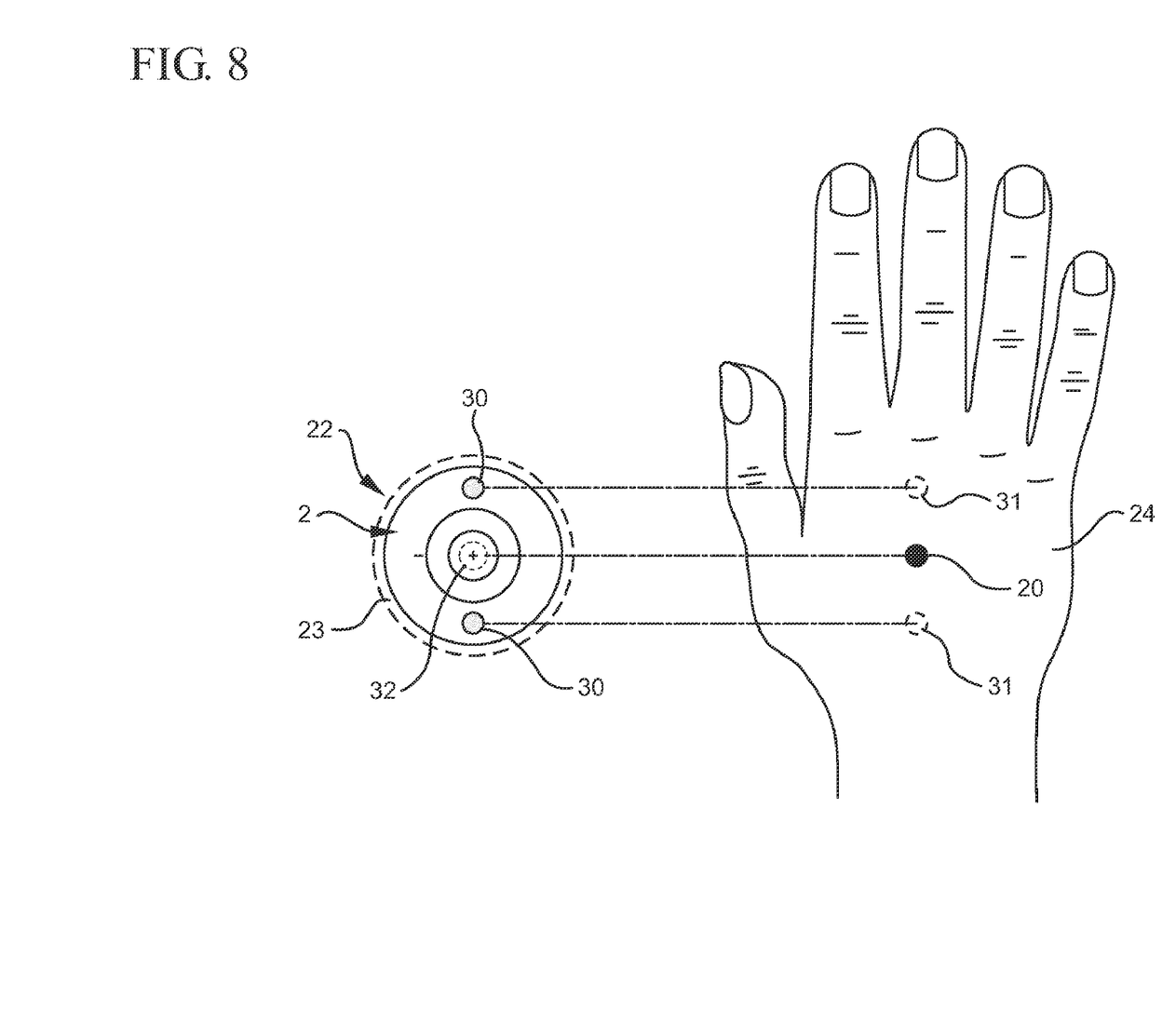
FIG. 8 is a bottom plan view of a concentric skin electrode patch constructed in yet another form of the present invention and illustrating its placement and affixation on a patient's skin for neurostimulation.

In a further embodiment of the present invention as depicted in FIG. 8, one or more metal discs 30 may be used as the securing means 27, and one or more magnets 31 are placed under the patient's skin 24. The magnets 31 are preferably encased within a biocompatible polymer casing (not shown). Attraction between the metal discs 30 and the magnets 31 keeps the concentric skin electrode patch 22 in place. This eliminates the need for adhesives 26 for securing the concentric skin electrode patch 22 to the patient's skin.

Figure 9:
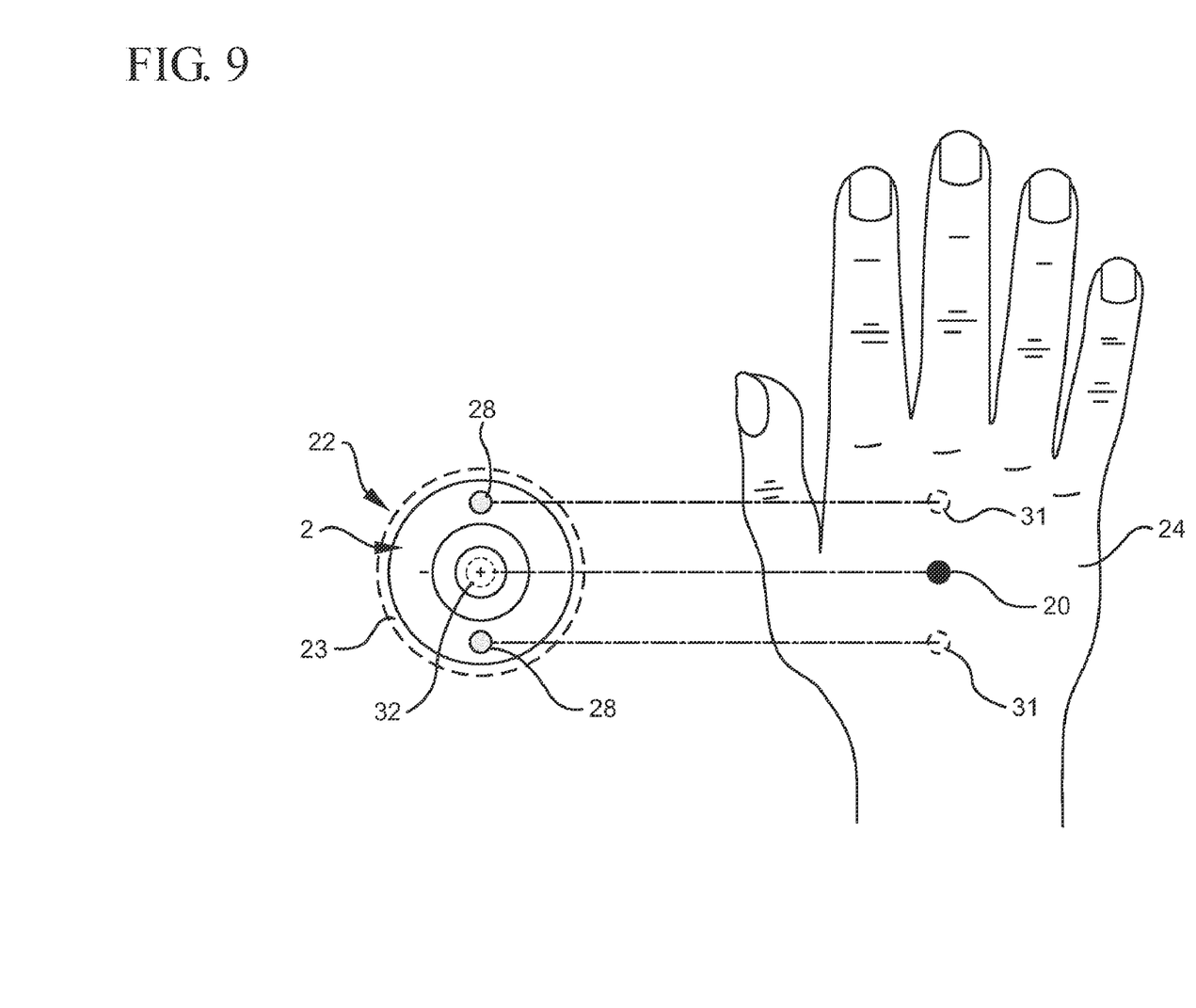
FIG. 9 is a bottom plan view of a concentric skin electrode patch constructed in yet another form of the present invention and illustrating its placement and affixation on a patient's skin for neurostimulation.

In yet another embodiment of the present invention as depicted in FIG. 9, if one or more magnets 28 are used as the securing means 27, one or more magnets 31 of opposite polarity are placed under the patient's skin 24. The magnets 31 placed under the skin are preferably encased within a biocompatible polymer casing (not shown). Attraction between the patch magnets 28 and the implanted magnets 31 keeps the concentric skin electrode patch 22 in place. This eliminates the need for adhesives 26 for securing the concentric skin electrode patch 22 to the patient's skin.

Figure 10:
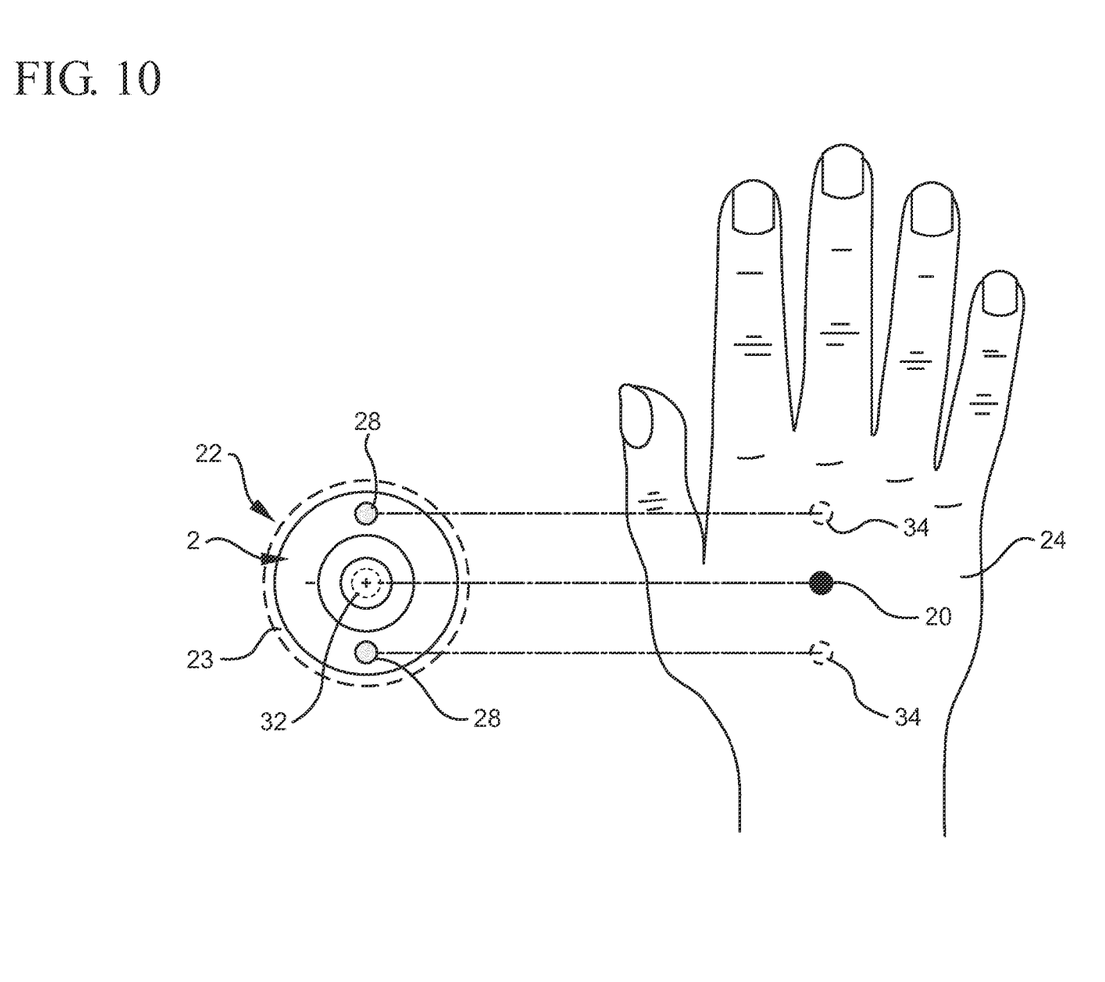
FIG. 10 is a bottom plan view of a concentric skin electrode patch constructed in yet another form of the present invention and illustrating its placement and affixation on a patient's skin for neurostimulation.

In yet another embodiment of the present invention as depicted in FIG. 10, if one or more magnets 28 are used as the securing means 27, one or more discs 34 made from metal or other magnetically attractable material are placed under the patient's skin 24. The metal discs 34 are preferably encased within a biocompatible polymer casing (not shown). Attraction between the magnets 28 and the metal discs 34 keep the concentric skin electrode patch 22 in place. This eliminates the need for adhesives 26 for securing the concentric skin electrode patch 22 to the patient's skin.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An electrode patch used for identifying a location on a patient's skin for placement of a neurostimulation electrode patch on the patient's skin to stimulate a nerve, which comprises:
    a supporting structure;
    an array of electrodes mounted on the supporting structure, each electrode of the array of electrodes having a cathode and an anode and being spaced apart from each other on the supporting structure;
    the patch being placeable on a patient's skin, each electrode of the array of electrodes being individually energizable to determine the location for placement of the neurostimulation electrode patch on the patient's skin to stimulate the nerve; and
    a stimulation generator mounted on the supporting structure, the stimulation generator being electrically coupled to each of the electrodes of the array of electrodes and generating a signal including a controlled, amplitude-modulated waveform adapted for stimulating nerves, each electrode of the array of electrodes being individually energizable by the signal generated by the stimulation generator, wherein each of the individual electrodes is energized sequentially and out of phase from the other electrodes of the array of electrodes to generate a stimulation pattern to detect and locate the nerve to be stimulated.

2. An electrode patch as defined by claim 1, which further comprises:
    a power source mounted on the supporting structure.

3. An electrode patch as defined by claim 1, wherein the supporting structure includes a flexible printed circuit.

4. An electrode patch as defined by claim 1, wherein each electrode of the array of electrodes is a circular electrode, and wherein the cathode is centrally located on the electrode and the anode is positioned to concentrically surround the cathode.

5. An electrode patch as defined by claim 1,
wherein each electrode of the array of electrodes is a circular electrode, and
wherein the anode is centrally located on the electrode and the cathode is positioned to concentrically surround the anode.

6. A method of identifying a location on a patient's skin for placement of a neurostimulation electrode patch on the patient's skin to stimulate a nerve, which comprises the steps of:
placing an electrode patch on the patient's skin, the electrode patch including a supporting structure and an array of electrodes mounted on the supporting structure, each electrode of the array of electrodes having a cathode and an anode and being spaced apart from each other on the supporting structure; and
energizing each electrode of the array of electrodes sequentially and out of phase from the other electrodes of the array of electrodes for generating signals to stimulate the nerve and noting the patient's response when each electrode is energized to stimulate the nerve to determine the location for placement of the neurostimulation electrode patch on the patient's skin to stimulate the nerve.

* * * * *